(12) United States Patent
Volkar et al.

(10) Patent No.: US 11,107,570 B2
(45) Date of Patent: Aug. 31, 2021

(54) FLEXIBLE, EXTENSIBLE AND AUTOMATED SYSTEMS AND METHODS FOR SCORING THE QUALITY OF RADIOLOGY EXAMINATIONS

(71) Applicant: BAYER HEALTHCARE LLC, Whippany, NJ (US)

(72) Inventors: John Volkar, Valencia, PA (US); Corey A. Kemper, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 237 days.

(21) Appl. No.: 16/301,562

(22) PCT Filed: May 15, 2017

(86) PCT No.: PCT/US2017/032637
§ 371 (c)(1),
(2) Date: Nov. 14, 2018

(87) PCT Pub. No.: WO2017/200913
PCT Pub. Date: Nov. 23, 2017

(65) Prior Publication Data
US 2019/0214149 A1    Jul. 11, 2019

Related U.S. Application Data

(60) Provisional application No. 62/339,490, filed on May 20, 2016.

(51) Int. Cl.
*G16H 30/20* (2018.01)
*G16H 10/20* (2018.01)
(Continued)

(52) U.S. Cl.
CPC ............ *G16H 30/20* (2018.01); *G16H 10/20* (2018.01); *G16H 30/40* (2018.01); *G16H 50/70* (2018.01)

(58) Field of Classification Search
CPC .... G06F 1/00–2221/2153; G16H 10/00–80/00
See application file for complete search history.

(56) References Cited

U.S. PATENT DOCUMENTS

| | | |
|---|---|---|
| 5,583,902 A | 12/1996 | Bae et al. |
| 5,687,208 A | 11/1997 | Bae et al. |
| | (Continued) | |

FOREIGN PATENT DOCUMENTS

| | | | |
|---|---|---|---|
| CN | 102058432 | * | 5/2011 |
| WO | 2006055813 A2 | | 5/2006 |
| | (Continued) | | |

OTHER PUBLICATIONS

Ramanaidu et al., "Evaluation of radiation dose and image quality following changes to tube potential (kVp) in conventional paediatric chest radiography," Biomedical Imaging and Intervention Journal, 2(3): e35, pp. 1-10 (Year: 2006).*

(Continued)

*Primary Examiner* — Elaine Gort
*Assistant Examiner* — Jonathon A. Szumny
(74) *Attorney, Agent, or Firm* — James R. Stevenson; Byron Clark

(57) ABSTRACT

The present disclosure relates to automated systems and methods which assess the quality of radiology examinations and identify actionable changes to improve the quality of future exams. For each of a plurality of imaging studies, a study protocol and set of study metrics can be defined and the defined study protocol can be performed to generate data associated with the imaging study. A metrics assessment can be performed by applying at least a portion of the data associated with the result of the imaging study against the set of study metrics for the imaging study so as to generate a metrics score for the imaging study. The metrics scores can (Continued)

be stored in a score repository and analyzed so as to provide recommendations to improve the examination process.

11 Claims, 7 Drawing Sheets

(51) Int. Cl.
  *G16H 50/70* (2018.01)
  *G16H 30/40* (2018.01)

(56) References Cited

U.S. PATENT DOCUMENTS

| | | | |
|---|---|---|---|
| 6,055,985 | A | 5/2000 | Bae et al. |
| 6,470,889 | B1 | 10/2002 | Bae et al. |
| 6,635,030 | B1 | 10/2003 | Bae et al. |
| 7,421,647 | B2 | 9/2008 | Reiner et al. |
| 7,532,942 | B2 | 5/2009 | Reiner et al. |
| 7,593,549 | B2 | 9/2009 | Reiner et al. |
| 7,607,079 | B2 | 10/2009 | Reiner et al. |
| 7,831,445 | B2 | 11/2010 | Reiner et al. |
| 7,849,115 | B2 | 12/2010 | Reiner et al. |
| 7,853,476 | B2 | 12/2010 | Reiner et al. |
| 7,925,330 | B2 | 4/2011 | Kalafut et al. |
| 7,933,782 | B2 | 4/2011 | Reiner et al. |
| 8,018,487 | B2 | 9/2011 | Reiner et al. |
| 8,081,165 | B2 | 12/2011 | Reiner et al. |
| 8,117,549 | B2 | 2/2012 | Reiner et al. |
| 8,249,892 | B2 | 8/2012 | Reiner et al. |
| 8,301,461 | B2 | 10/2012 | Reiner et al. |
| 8,333,508 | B2 | 12/2012 | Reiner et al. |
| 8,335,694 | B2 | 12/2012 | Reiner et al. |
| 8,412,544 | B2 | 4/2013 | Reiner et al. |
| 8,538,776 | B2 | 9/2013 | Reiner et al. |
| 8,615,529 | B2 | 12/2013 | Reiner et al. |
| 8,655,677 | B2 | 2/2014 | Reiner et al. |
| 8,824,752 | B1* | 9/2014 | Fonte ............... A61B 6/481 382/126 |
| 8,856,188 | B2 | 10/2014 | Reiner et al. |
| 8,957,955 | B2 | 2/2015 | Reiner et al. |
| 2006/0274145 | A1* | 12/2006 | Reiner ............. G16H 30/40 348/62 |
| 2007/0213662 | A1 | 9/2007 | Kalafut et al. |
| 2007/0255135 | A1 | 11/2007 | Kalafut et al. |
| 2008/0097197 | A1 | 4/2008 | Kalafut et al. |
| 2008/0175460 | A1 | 7/2008 | Reiner et al. |
| 2010/0030073 | A1 | 2/2010 | Kalafut et al. |
| 2010/0113887 | A1 | 5/2010 | Kalafut et al. |
| 2010/0145720 | A1 | 6/2010 | Reiner et al. |
| 2010/0204572 | A1 | 8/2010 | Kalafut et al. |
| 2011/0270123 | A1 | 11/2011 | Reiner et al. |
| 2011/0282194 | A1 | 11/2011 | Reiner et al. |
| 2012/0078648 | A1 | 3/2012 | Reiner et al. |
| 2012/0166218 | A1 | 6/2012 | Reiner et al. |
| 2013/0006064 | A1 | 1/2013 | Reiner et al. |
| 2013/0253314 | A1 | 9/2013 | Kalafut et al. |
| 2013/0304508 | A1* | 11/2013 | Shah ............... G16H 10/60 705/3 |
| 2013/0311190 | A1 | 11/2013 | Reiner et al. |
| 2014/0221832 | A1* | 8/2014 | El-Zehiry ......... G16H 30/40 600/437 |
| 2014/0254897 | A1* | 9/2014 | Ferguson ............ G06T 7/001 382/128 |
| 2014/0358585 | A1 | 12/2014 | Reiner et al. |
| 2015/0100572 | A1 | 4/2015 | Kalafut et al. |
| 2016/0253461 | A1* | 9/2016 | Sohr ................ C25B 11/04 705/3 |
| 2017/0202534 | A1 | 7/2017 | Crotty et al. |
| 2018/0325481 | A1* | 11/2018 | Young ............... G16H 50/30 |
| 2019/0066297 | A1* | 2/2019 | Middlebrooks ....... G06T 7/0016 |

FOREIGN PATENT DOCUMENTS

| | | |
|---|---|---|
| WO | 2006058280 A2 | 6/2006 |
| WO | 2006116700 A2 | 11/2006 |
| WO | 2008085421 A2 | 7/2008 |

OTHER PUBLICATIONS

"International Preliminary Report on Patentability from PCT Application No. PCT/US2017/032647", dated Nov. 29, 2018.

"International Search Report and Written Opinion from PCT Application No. PCT/US2017/032637", dated Aug. 18, 2017.

\* cited by examiner

Quality Metrics

*Select the metrics that apply:*

☑ Scan Range

From [Thoracic Inlet ▾]

To   [Lowest Diaphragm ▾]

☑ No Streak Artifact

☑ Minimum Enhancement

ROI [Pulmonary Trunk ▾]

Greater than [250] HU

[Add ROI...]

☑ Maximum Enhancement

ROI [Pulmonary Trunk ▾]

Less than [400] HU

[Add ROI...]

☑ Comparative Enhancement

[Pulmonary Trunk ▾] [> ▾]

[Aorta ▾]

☐ Contrast to Noise Ratio

Greater than [ ]

☑ Exam Duration

(Last Acquisition End) - (First Acquisition Start)

Less than [5] min

☑ Radiation Dose

DLP Less than [200] mGy-cm

☑ Number of Injections

Equal to [1]

☑ Catheter Usage

Is [18ga, 20ga, 22g ▾]

☐ Injection Site

Is [Select... ▾]

☑ Delivered Flow Rate

[> ▾] [4.0] ml/s

☐ Delivered Contrast Volume

Exam Scorecard

John Doe (65yo M, exam on 15 Mar 2016)

Scan Range: 👍
   From  Thoracic Inlet
   To    Lowest Diaphragm

No Streak Artifact 👍

Minimum Enhancement 👎
   Pulmonary Trunk

Maximum Enhancement 👍
   Pulmonary Trunk

Comparative Enhancement 👍
   Pulmonary Trunk > Aorta

Exam Duration 👍
   Less than 5min

Radiation Dose 👍
   DLP less than 200 mGy-cm

Number of Injections 👍
   Equal to 1

Catheter Usage 👍
   One of: 18ga, 20ga, 22ga

Delivered Flow Rate 👎
   Greater than 4.0ml/s

FIG. 5

FLEXIBLE, EXTENSIBLE AND AUTOMATED SYSTEMS AND METHODS FOR SCORING THE QUALITY OF RADIOLOGY EXAMINATIONS

CROSS REFERENCE TO RELATED APPLICATION

This application claims the benefit of U.S. Provisional Patent Application Ser. No. 62/339,490, filed May 20, 2016, the entire contents of which are hereby incorporated by reference.

BACKGROUND OF THE INVENTION

Field of the Invention

The present disclosure relates to automated quality assessment systems and methods. More particularly, the present disclosure relates to systems and methods which assess and improve upon the quality of radiology examinations.

Description of Related Art

The following information is provided to assist the reader to understand the environment in which the methods and systems of the present disclosure will typically be used. Specific terms used herein are not intended to be limited to any particular narrow interpretation unless clearly stated otherwise in this document. The disclosure of all references cited herein is incorporated by reference.

In the field of radiology, there has been an increased attention in recent years to understanding, assessing, and quantifying "image quality." While "image quality" is a key goal, it is difficult to define and even more difficult to quantify. Realistically, what is needed is an image set that provides sufficient information to enable the correct diagnosis but also minimizes the amount of radiation (depending on modality) and contrast dose (for contrast enhanced imaging). That does not necessarily correspond to what is perceived as the best quality image. For example, prior to concern over the potential long-term health impacts of radiation, beautiful images with high signal-to-noise-ratio (SNR) were considered to be high quality. Now, there is a desire to instead balance quality against dose. Calculating dose is relatively straightforward, but quality metrics are much more challenging.

Determining whether an image is a "good" image is further complicated by the fact that there are aspects of the image that are completely out of the radiologist's or technologist's control. For example, with the same imaging parameters, a larger patient will have a noisier image than a smaller one. Is the right choice to try to match the signal-to-noise across the entire population, even if it means that larger patients will receive more radiation? Similarly, what if the reason for the higher radiation dose is not that the technologist increased the tube current to minimize the noise but used a larger scan range than was defined by the imaging protocol? In this case, the SNR is the same, but the dose is unnecessarily higher. Similarly, scanner manufacturers have introduced technology to try to optimize the quality of the image against the dose delivered. One of these is tube current modulation, where in areas where less radiation is needed, less is delivered and vice versa. When it is not used, the overall dose may be the same but the image will be worse. For contrast enhanced imaging, the appropriate contrast dose will affect the brightness of the image, and while it is possible to measure a contrast to noise ratio (CNR), the enhancement level will be affected by the patient (cardiac output, blood volume, etc.), the contrast dose and delivery rate, the timing of the scan acquisition, and other modality-dependent imaging parameters (e.g. tube voltage).

Simply plotting dose against SNR and trying to find the optimal point does not address any of these issues in the actual quality of the examination. Some hospitals have implemented quality control programs that may include manual review, where images are evaluated to see if the scan range was correct, if the protocol was followed, etc. This is time-consuming and can only reasonably be done on a small subset of studies.

In essence, examination quality is more than image quality. Examination quality is built up from quantifiable things, mixed and weighted as desired. It is more holistic in nature in that it can include appropriateness, compliance with policies, procedures and protocols, as well as the quality of the resulting image. In this sense, the focus on image quality is shortsighted since it does not take into proper consideration the overall quality of the examination or otherwise focus on what aspects make an exam "good" beyond the quality of the image that results therefrom.

It is against this backdrop that the utility and advantages of the systems and methods described herein become readily apparent.

SUMMARY

In accordance with some aspects, described is a method for generating an updated study protocol. The method includes defining a study protocol and a set of study metrics for each of a plurality of imaging studies, performing the defined study protocol so as to generate data associated with a result of the imaging study, performing a metrics assessment by applying the data against the set of study metrics so as to generate a metrics score, reviewing, at a reviewing unit, one or more of the metrics scores, and based on the review of the one or more metrics scores, generating an updated study protocol.

In accordance with other aspects, described is a system that includes one or more protocol units that can define a study protocol and a set of study metrics for each of a plurality of imaging studies, a score repository comprising a set of database entries associated with the plurality of imaging studies, one or more scoring units that can perform metrics assessments, and one or more reviewing units that display a visually perceptible summary of one or more of the metrics scores on a display screen associated with the reviewing unit.

Various aspects of the present disclosure may be further characterized by one or more of the following clauses:

Clause 1. A method, comprising: for each of a plurality of imaging studies, defining, at a protocol unit, a study protocol; for each of the plurality of imaging studies, defining, at the protocol unit, a set of study metrics; for each of the plurality of imaging studies, performing the defined study protocol so as to generate data associated with a result of the imaging study; for each of the plurality of imaging studies, performing, by a scoring unit, a metrics assessment by applying at least a portion of the data associated with the result of the imaging study against the set of study metrics for the imaging study so as to generate a metrics score for the imaging study, wherein the metrics score for each of the plurality of imaging studies is stored in a score repository; reviewing, at a reviewing unit, one or more of the metrics scores stored in the score repository; and based on the review of the one or more metrics scores, generating an updated study protocol.

Clause 2. The method of clause 1, wherein the study protocol comprises a set of criteria regarding how to conduct a study protocol.

Clause 3. The method of clause 1 or 2, wherein the set of study metrics comprises a list of quantifiable characteristics of the study and the results thereof.

Clause 4. The method of any of clauses 1-3, wherein defining the set of study metrics comprises selecting a plurality of study metrics from a list of available study metrics.

Clause 5. The method of clause 4, wherein defining the set of study metrics further comprises providing, for each of the plurality of study metrics, a metric evaluation criteria.

Clause 6. The method of any of clauses 1-5, wherein reviewing one or more of the metrics scores stored in the score repository comprises reviewing a visually perceptible summary of the metrics scores for at least one of the imaging studies.

Clause 7. The method of clause 6, wherein the visually perceptible summary of the metrics score comprises a set of binary indicators, wherein each binary indicator is associated with a study metric.

Clause 8. The method of any of clauses 1-7, wherein reviewing one or more of the metrics scores stored in the score repository comprises reviewing, at the reviewing unit, an aggregate of the metrics scores from a plurality of the imaging studies.

Clause 9. The method of clause 8, further comprising modifying one or more of the study metrics so as to cause an updated aggregate of the metrics scores to be created by the scoring unit.

Clause 10. The method of clause 9, further comprising reviewing, at the reviewing unit, the updated aggregate of the metrics scores.

Clause 11. The method of any of clauses 1-10, wherein the plurality of imaging studies are selected from the group consisting of computerized tomography imaging studies, positron emission tomography imaging studies, molecular imaging studies, ultrasound imaging studies, and magnetic resonance imaging studies.

Clause 12. A method, comprising: receiving, at a score repository, data related to a plurality of imaging studies, wherein the data related to the plurality of imaging studies comprises, for each of the plurality of imaging studies, a study protocol, a set of study metrics, and data associated with a result of the imaging study; performing, by a scoring unit, a metrics assessment for each of the plurality of imaging studies by applying at least a portion of the data associated with the result of the imaging study against the set of study metrics for the imaging study so as to generate a metrics score for the imaging study; receiving, at a reviewing unit, a visually perceptible summary of the metrics score for at least one of the plurality of imaging studies; and presenting, on one or more display screens, the visually perceptible summary of the metrics score for the at least one of the plurality of imaging studies.

Clause 13. The method of clause 12, further comprising: generating, by the scoring unit, an aggregate of the metrics scores comprised of a plurality of the metrics scores; receiving, at the reviewing unit, a visually perceptible summary of the aggregate of the metrics scores; and presenting, on one or more display screens, the visually perceptible summary of the aggregate of metrics scores.

Clause 14. The method of clause 13, further comprising: receiving, at the scoring unit, a request to modify one or more of the study metrics used to generate one or more of the metrics scores included in the aggregate of the metrics scores; generating, by the scoring unit, one or more updated metrics scores by applying at least a portion of the data associated with the result of the imaging study against at least the one or more modified study metrics; and generating, by the scoring unit, an updated aggregate of the metrics scores comprised of at least the updated metrics scores.

Clause 15. The method of clause 14, further comprising: receiving, at the reviewing unit, a visually perceptible summary of the updated aggregate of the metrics scores; and presenting, on one or more display screens, the visually perceptible summary of the updated aggregate of the metrics scores.

Clause 16. The method of any of clauses 12-15, wherein the study protocol comprises a set of criteria regarding how to conduct a study protocol.

Clause 17. The method of any of clauses 12-16, wherein the set of study metrics comprises a list of quantifiable characteristics of the study and the results thereof.

Clause 18. The method of any of clauses 12-17, wherein the visually perceptible summary of the metrics score comprises a set of binary indicators, wherein each binary indicator is associated with a study metric.

Clause 19. A system, comprising: one or more protocol units, wherein each of the protocol units has associated therewith a non-transitory, computer readable medium containing a set of programming instructions that, when executed by a processor, permit the protocol unit to define, for each of a plurality of imaging studies, a study protocol and a set of study metrics; a score repository comprising a set of database entries, wherein each database entry is associated with one of the plurality of imaging studies and comprises a study protocol, a set of study metrics, and data associated with a result of the imaging study; one or more scoring units, wherein each of the scoring units has associated therewith a non-transitory, computer readable medium containing a set of programming instructions that, when executed by a processor, permit the scoring unit to perform, for each of the plurality of imaging studies, a metrics assessment by applying at least a portion of the data associated with the result of the imaging study against the set of study metrics for the imaging study so as to generate a metrics score for the imaging study; and one or more reviewing units, wherein each of the reviewing units has associated therewith a non-transitory, computer readable medium containing a set of programming instructions that, when executed by a processor, permit the reviewing unit to display a visually perceptible summary of one or more of the metrics scores on a display screen associated with the reviewing unit.

Clause 20. The system of clause 19, wherein the programming instructions contained in the computer-readable medium associated with the one or more scoring units, when executed by a processor, further permit the scoring unit to prepare an aggregate of the metrics scores comprised of a plurality of the metrics scores.

These and other features and characteristics of the methods and systems, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE FIGURES

The Figures associated with the present disclosure describe specific embodiments and should not be considered limiting to the overall disclosure as set forth in the claims.

FIG. 3 is a representation of a partial listing of metrics and metric values according to one non-limiting embodiment;

FIG. 5 is a representation of a metrics score presented as a visually perceptible scorecard according to one non-limiting embodiment;

DETAILED DESCRIPTION

Figure 1:
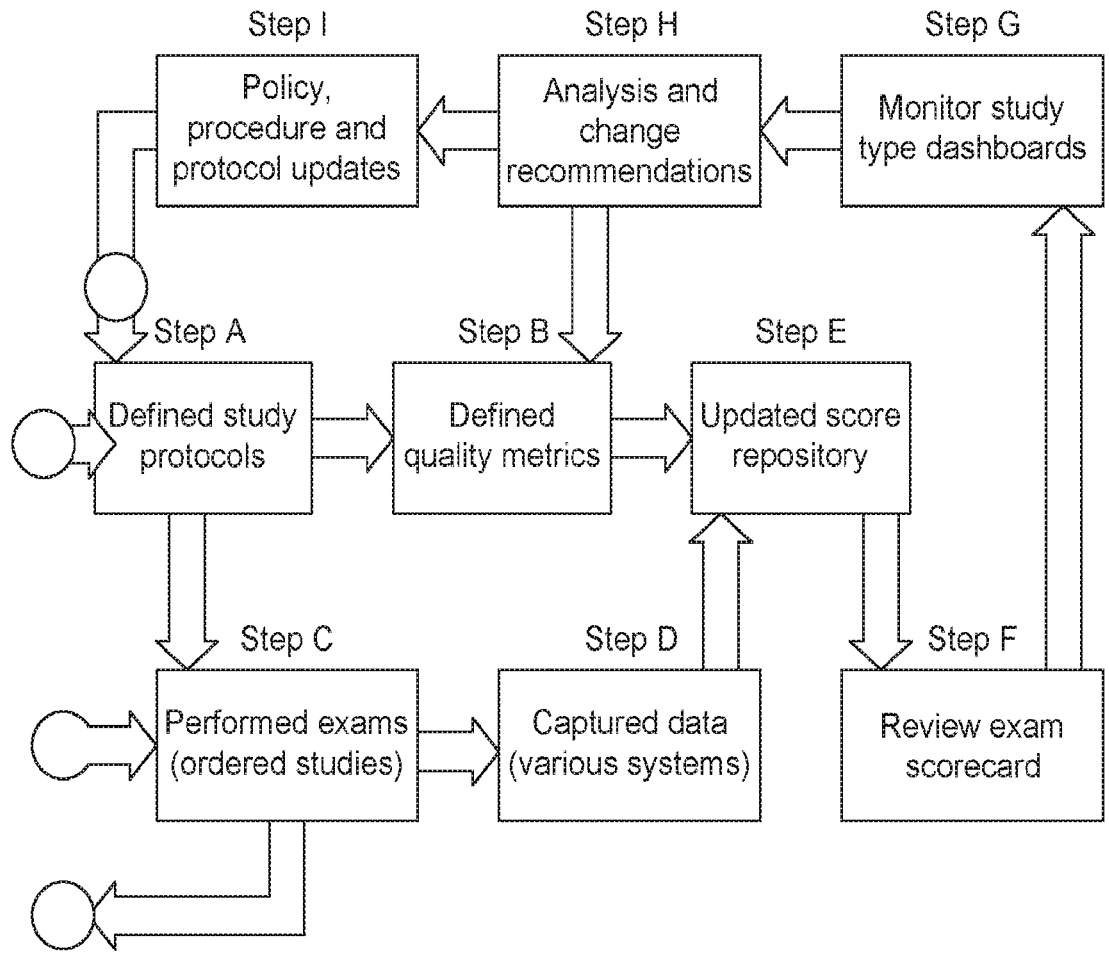
FIG. 1 is a flowchart of a method for defining and assessing a set of metrics for one or more radiological studies according to one non-limiting embodiment.

The illustrations generally show preferred and non-limiting aspects of the present disclosure. While the descriptions present various aspects of the systems and/or methods described herein, it should not be interpreted in any way as limiting the disclosure. Furthermore, modifications, concepts, and applications of the disclosure's aspects are to be interpreted by those skilled in the art as being encompassed by, but not limited to, the illustrations and descriptions provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, processed, routed, etc., between the first and second unit or device. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. For instance, data communicated from one component to another can pass through one or more nodes, which can serve as a local data collection and communication module performing functionality commonly associated with a networked system, such as "store and forward" and other low-level data collection, processing and communication functions. It will be appreciated that numerous other arrangements are possible. Throughout this description and in the figures, communication links from one component to another will be discussed and illustrated. For clarity, the arrows indicate the direction of the communication. The arrows may be understood to indicate separate, one-way communication links. Alternatively, they may indicate a single communication link that facilitates two-way communication. As would be appreciated by those skilled in the art, the communication link(s) may be a telephone line, a wireless communication link, or the Internet, among others.

Various embodiments of this disclosure relate to automated systems and methods for generating an actionable score for a medical study through the use of one or more metrics related to the results of the medical study. The metrics comprise a set of values related to certain characteristics of the study and the results thereof and can be applied against the data generated during the study to ascertain whether those characteristics of the study and the results thereof have been satisfied. While not limited thereto, this disclosure focuses on medical imaging studies, such as computerized tomography (CT), positron emission tomography (PET), molecular imaging (MI), ultrasound imaging, and magnetic resonance imaging (MRI) in which a medical image of a patient is generated. The metrics that are discussed herein are generally those characteristics of the study and the results thereof for which a certain value is desired. The systems and methods discussed herein can tie together different aspects into an actionable score for an individual examination providing flexible, extensible, and automated systems and methods that can offer a holistic assessment of the quality of an examination beyond, and even separate from, the quality of the image itself.

FIG. 1 is a flowchart illustrating various steps, stages, or phases that may be present in an exemplary process according to this disclosure. The flowchart includes steps of defining a study protocol for an imaging study, defining the study metrics for the study, completing the study by following the criteria set forth in the study protocol, performing a metrics assessment of the study by applying data related to the study to the study metrics so as to create a metrics score for the study, creating a database entry for the study in a score repository, accessing data stored in the score repository for purposes of analyzing and/or improving upon the effectiveness of one or more study protocols, and performing one or more studies using an improved study protocol. The flowchart is provided to facilitate understanding of the various embodiments of the invention that will now be disclosed. The various systems and methods described hereinafter are generally applicable to the process outlined in FIG. 1. Exemplary data communications are shown with arrows in FIG. 1.

Figure 2:
FIG. 2 is a representation of a portion of a study protocol according to one non-limiting embodiment.

At Step A, a study protocol is defined. For purposes of this disclosure, a study protocol is a structured set of criteria to guide a technologist or other individual on how to conduct a certain imaging study using study equipment, such as an injector and a scanner. When defining a study protocol, a variety of data elements are created and documented. Included among the data elements are the sequence of the injection and/or scanner acquisition steps and the technical parameters of each. For example, if an injection or multiple injections are involved, the number of phases and the volume(s) and flowrate(s) associated with each phase are data elements that are created and documented. For scanner acquisitions, the tube voltage (kVp) and current (mAs) are notable data elements that are created and documented. Many other data elements are created and documented for a study protocol, as would be appreciated by one of skill in the art upon reading this disclosure. FIG. 2 represents a portion of an exemplary protocol.

Methods of defining a study protocol are well known in the art. For example, defining a study protocol could involve selecting a pre-existing study protocol that has been used in the past on similar patients. Such protocols can be recalled from memory associated with the study equipment, such as memory associated with the scanner or injector, or they may be electronically stored elsewhere on a network accessible by the study equipment, such as on a website or in a central repository. Study protocols can be pushed to the study equipment automatically, or retrieved by the equipment upon command. As yet another alternative, the study protocols can be stored on physical media, such as in a binder or in a notebook, and the criteria that form the study protocol can be manually entered into the study equipment by the technician. Defining a study protocol could also involve the use of one or more protocol prediction and/or modeling techniques known in the art, such as those described in U.S. Pat. Nos. 5,583,902, 5,687,208, 6,055,985, 6,470,889 and 6,635,030, and 7,925,330, U.S. Pat. App. Pub. Nos. 2007/0213662, 2007/0255135, 2008/0097197, 2010/0030073, 2010/0113887, 2010/0204572, 2013/0253314, and 2015/0100572, and PCT App. Pub. Nos. WO/2006/058280, WO/2008/085421, and WO/2006/055813, the disclosure of each of which is incorporated herein by reference and made a part hereof.

At Step B, which can coincide with Step A, the metrics associated with the study can be defined. Defining the metrics for a study can include selecting which metrics should be included for the study and setting the values for each metric. The systems and methods described herein can be designed to allow for flexibility in selecting the metrics for a given study so as to permit a user to customize the number, type and configuration of the scoring mechanism. FIG. 3 illustrates a partial listing of exemplary metrics and metric values that can be presented on a display screen and selected from for purposes of defining the metrics of the study through the use of radio buttons, drop down menus, and text fields. In FIG. 3, the selected metrics include "scan range," "no streak artifact," exam duration," "delivered flow rate," and others. The metric values are, for example, "from thoracic inlet to lowest diaphragm" for the scan range metric, "less than 5 min." for the exam duration metric, and "greater than 4.0 ml/s" for the delivered flow rate metric. The metric value for some metrics, such as "no streak artifact," is simply whether or not the metric has been selected. FIG. 3 also illustrates certain metrics that, while available, were not selected, such as "contrast to noise ratio" and "delivered contrast volume." This list is not intended to be complete or limiting. One of skill in the art, upon reading this disclosure, would be able to identify on the order of 100 metrics related to the examination (including proper techniques, contrast agents used, equipment operating parameters, recordkeeping functions, etc.) that could be used with the systems and methods described herein.

It would also be appreciated that not every metric would be relevant for a particular study or study type. For example, metrics related to an injection phase of the study, such as injection site or number of injections, would not be relevant if the study does not involve an injection phase. To streamline the selection process, the metrics can be grouped according to relevance or relatedness. For example, the metrics related to an injection phase can be grouped together so that they can be easily addressed sequentially. By way of another example, the metrics most relevant to a CT study can be grouped together. The available metrics can also be initially filtered based on, for example, the study type, so that only those metrics that are potentially relevant to the study type at issue are available for selection. For example, if the study will be a CT study, only those metrics potentially relevant to a CT study can be presented. Similarly, the available metrics can be initially filtered based on patient type. For example, if the patient is one who is at risk of experiencing contrast induced nephropathy, metrics related to the total volume of contrast can be presented. The metrics can also come pre-selected based on, for example, the study type, patient type, or imaging modality. For example, for a CT pulmonary angiography study, the list of metrics could be presented with those metrics that are generally considered relevant to this type of study already selected and recommended metric values already filled in. By way of another example, if a certain study protocol is selected, such as a protocol that has been assigned Protocol Number 23AB by a doctor or other medical personnel, the metric list could be presented with the metrics and values previously defined for this protocol already provided. By way of yet another example, if setting up a study protocol to be used specifically for patients at risk of experiencing contrast induced nephropathy, the total volume of contrast metric can be pre-selected and provided with a metric value that has been determined to be appropriate for this category of patients. In an embodiment where the metrics and/or values are pre-selected, the reviewer can also have the option to unselect certain metrics, to select additional metrics, and to modify the metric values as he or she deems appropriate. Of course, it is also possible to present a "clean slate" of all possible metrics without any values filled in to allow the reviewer maximum autonomy in defining the metrics for a study.

Defining the metrics for a study can take into account the relative importance of the metric and the ability to collect usable data related thereto. For example, one of the most broadly applicable criteria is scan range since the primary point of an imaging procedure is to obtain an image of a particular part of the body. If the wrong area has been scanned, no matter how high quality the image, it was a poor quality exam. Thus, scan range can be a selected metric. In choosing a value for this metric, one must consider the desired range of the scan for the study. For example, for a CT pulmonary angiography, the range could be defined as thoracic inlet to lowest diaphragm. This range could be set as the metric value. When the study is performed, the study is usually tagged with a study description corresponding to the pre-defined protocol. In a post-processing step, the acquisition can be analyzed to assess the scan range using existing algorithms for landmark detection to see if that particular patient was over or under scanned. Thus, scan range is both important and automatically measurable, and could be selected as a study metric on this basis.

By way of another example, various dose reduction techniques may be suitable study metrics. For instance, if the protocol has been defined to include tube current modulation, post-processing of the DICOM image headers will show if the technologist did in fact turn tube current modulation on. Similarly, if the technologist is to reduce the tube voltage if the patient is less than a certain size, this can be easily tracked as well. By way of yet another example, for contrast enhanced imaging, especially CT, there is often a target level of enhancement that is desired in a particular region of interest. Again, with existing techniques to segment blood vessels, the peak enhancement can be readily compared to a target value. In addition, for first pass imaging, timing is critical. Streak artifact is relatively easy to detect automatically and often signals that the scan was performed too early relative to the end of the injection. Still further, for power injected studies, there is instruction for what catheter to use. With existing injection logging systems, a comparison of the catheter gauge to what was recommended can also be done. By way of yet another example, the presence of secondary capture images in specific series can be a means to confirm that patient consent/interview data was obtained and is on record, providing an automated way of checking on a manual paper process. All of the above are good candidates for study metrics because they are both important in assessing the quality of the study and they can be easily and automatically assessed through an analysis of the data that is generated and tracked during an imaging study.

The list of available metrics may be created at a central terminal and communicated to one or more protocol units that are used to define the study protocols and the metrics related thereto. Alternatively, the list of available metrics may be stored local to the protocol unit. In either case, the metric list can be updated to add new metrics. In this sense, the metric list and the underlying program that controls it are said to be extensible. Possible reasons for the addition of new metrics would be the existence of research studies that have discovered additional criteria that are believed to be important to a certain study type, the advent of study equipment such as scanners or injectors that are capable of generating and/or measuring additional types of data, and new techniques for extracting additional data from study results such as scanner images. Similarly, the metric list can be updated to delete existing metrics that, for example, are rarely used or which are deemed to be unimportant.

For purposes of this disclosure, the metrics selected for a particular study and the values thereof are referred to as the "study metrics." For reasons that will become apparent below, the metrics that are available for selection should be ones that can be automatically scored without requiring human interpretation or intervention, such as through a comparison of a measured value or values for a particular characteristic with a metric which places a quantitative limit or limits on the value for that characteristic. For example, a metric defining the flow rate as "greater than 4.0 ml/s" can be automatically assessed by extracting data on the flow rate value and comparing that data with the flow rate limit set by the metric. Similarly, a metric defining the number of injections as "equal to 1" can be automatically assessed by analyzing data generated by the injector. On the other hand, "image quality" is a metric that is typically difficult to automatically assess as it requires some amount of subjective human input. However, there are metrics related to image quality, such as signal-to-noise ratio values, that can be automatically determined through a computational analysis of the image that is generated from an imaging study.

Figure 4:
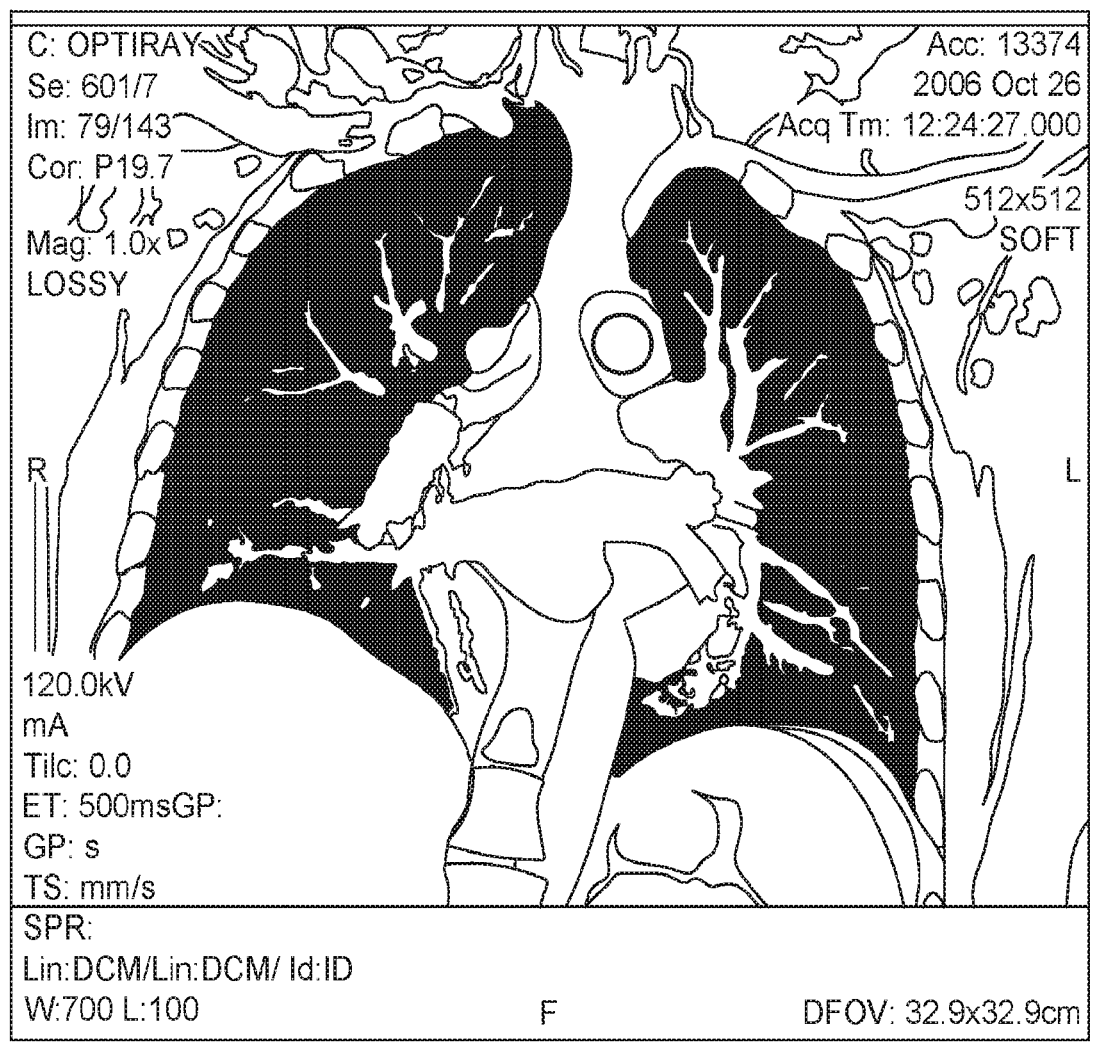
FIG. 4 is a representation of a single image from an image set of an exemplary study according to one non-limiting embodiment.

At Step C, the study is ordered, the study protocol is loaded into the examination equipment, such as, for example, the scanner and injector, the study begins by following the protocol, and the study ends. At Step D, a host of data related to the study is captured. This data can include data generated before, during, and after the study is performed. For example, this data can include data entered into the radiology information system (RIS) when the study is ordered, the set of images that were acquired by the scanner including the DICOM headers, and the injection data generated by the injector. FIG. 4 is a single image from an image set of an exemplary study. The full set of 3D images would also available for processing, including all series and reconstructions/projections. Image processing algorithms exist that can segment anatomy and extract specific measurements from the image sets. Step D can also involve communicating data from the study to existing systems, such as RIS, the picture archiving and communication system (PACS), the hospital information system (HIS), the electronic medical record (EMR), etc.

At Step E, the study metrics can be used to assess the quality of the study and generate a new entry in the score repository. In this step, a metrics assessment algorithm can be used to apply the study metrics against data generated from the study, such as text, image data, reconstructed images, as well as other data concerning the study, such as data that may be electronically stored in, for example, the RIS, PACS, or EMR, to assess how the data matches up with the metrics. For purposes of this disclosure, the process of applying the metrics against the data from the study is referred to as the "metrics assessment" for the study and the result of the metrics assessment is referred to herein as the "metrics score" for the study. In one non-limiting embodiment, the metrics assessment algorithm is a set of programming instructions stored on a non-transitory computer-readable medium that, when executed by a processor, permit the processor to perform the functions described in the programming instructions, including generating a metrics score for the study.

The metrics assessment process can be performed in a variety of ways. In one non-limiting embodiment, the data necessary to complete the metrics assessment process is automatically extracted from one or more databases where the data is stored. This data may include data generated by the study (e.g., the data output by the injector and/or scanner that were used to perform the study), pre-existing patient data (e.g., a patient's name, age, weight, etc. that may be stored in the HIS), and any other relevant information about the patient and/or the study that may have been collected before, during, or after the study, including data stored in PACS and/or RIS. Typically, the data is communicated from the one or more databases to the unit or units where the metrics assessment process will be performed across a network using standard file transfer protocols. In this context, the "extraction" of data also includes the communication of data directly from a data source to the unit or units performing the metrics assessment without first storing the data in an intermediate database. For example, the scanner and/or injector may be programmed to, upon completion of a study, automatically communicate some or all of the data generated during the study to the unit or units where the metrics assessment will be performed. This data transfer may be in addition to the standard data transfer rules in place that, for example, may require data generated by the scanner and/or injector to be communicated to other locations, such as PACS and/or RIS. The metrics assessment process also involves receiving the study metrics for the study in question. This can be provided in the same general manner as described above, including by communicating the study metrics across a network.

Once the study and/or patient data and the study metrics have been received, the study metrics can be applied against the data to determine which of the study metrics were satisfied and which of the study metrics were not satisfied. This process can be a straightforward comparison of the data associated with a certain characteristic of the study (e.g., the measured flow rate for the injection or the tube voltage applied by the scanner) with the corresponding study metric (e.g., the flow rate metric or the tube voltage metric). The process can be automated so as not to require human intervention to extract the data or apply the data against the study metrics. This process can be time consuming and use of automated procedures to generate the metrics scores can facilitate a larger number of studies being assessed. However, it is also envisioned that spot checking certain metrics scores by a human reviewer can be completed so as to ensure the metrics assessment process is operating correctly. This process can continue for all of the study metrics, or at least for each of the study metrics for which there is data available, until a score is assigned to each of the study metrics. The output of this process is the metrics score for the study, which can be in the form of a plurality of score/metric pairings with each metric having a score associated with it. In one non-limiting embodiment, the score for a metric may be a simple binary (e.g., "pass/fail") score, meaning the score for that metric simply indicates that the metric was either satisfied (metric value met) or unsatisfied (metric value not met). In another non-limiting embodiment, the score for a metric may be a relative score, meaning that the score for that metric provides an indication of not only whether or not the metric was satisfied, but also how close to the metric value the result was. Certain metrics lend themselves to having a binary score whereas others lend themselves to having a relative score. However, it is currently believed that binary scores are more advantageous for the reasons that are discussed elsewhere in this disclosure. The metrics score for the study can be comprised of a variety of different scoring types (e.g., some binary and some relative) or the metrics score for the study can be comprised of a single scoring type (e.g., all binary scores or all relative scores).

After the metrics assessment process is complete, the metrics score can be stored in the score repository where a new entry, such as a new database record, can be created for the study. The entry can include the details of the study, including the patient information, the protocol criteria, and the data generated by the study, as well as the list of metrics defined for the study and the metrics score generated through the metrics assessment process described above. As will be described below, this data can be extracted and used for various purposes.

With reference to Step F of FIG. 1, one manner in which the metrics score can be used is to present the metrics score in a visually perceptible form which can then be reviewed by a doctor, technician, hospital review board, or other qualified individual. In one non-limiting embodiment, the metrics score can be presented as a "scorecard" which summarizes the results of the metrics assessment in an easily understandable manner. An example of such a scorecard is illustrated in FIG. 5. With reference to FIG. 5, the scorecard shown therein provides a summary of the study, including the patient name, age, and sex, and the date of the exam, and provides the results of the metric assessment as a set of binary indicators. The binary indicators provide a straightforward assessment of whether each of the study metrics was, or was not, satisfied. For example, with reference to FIG. 5, the "thumbs up" icon for the "scan range" metric indicates that application of the scan range metric to the scan range data for the study revealed that the scan range metric was satisfied. In this case, the scan range metric was defined as "from the thoracic inlet to the lowest diaphragm," and thus it can be readily inferred from the "thumbs up" icon that the range of the scan was from the thoracic inlet to the lowest diaphragm. In contrast, the "thumbs down" icon for the "delivered flow rate" metric indicates that application of the flow rate metric to the flow rate data for the study revealed that the flow rate metric was not satisfied. In this case, the flow rate metric was defined as "greater than 4.0 ml/s," and thus it can be readily inferred from the "thumbs down" icon that the flow rate for the study was not greater than 4.0 ml/s. The visual display allows the individual reviewing the scorecard to draw these inferences without having to sort through the data generated by the study. Similar inferences about the other metrics can be drawn from the icons associated with the other metrics depicted on FIG. 5.

The "thumbs up" and "thumbs down" icons are only intended to be exemplary, and other graphics or means of indicating a metric's result could also be used. By way of example, a color coded system where green indicates that the metric was satisfied while red indicates that the metric was not satisfied could be used. In another example, another icon, such as a plus sign ("+") could be used to indicate that a metric has been satisfied while a minus sign ("−") could be used to indicate that a metric has not been satisfied. In addition, scoring types other than binary scoring could be used, as discussed above. However, reporting the metrics score in a binary manner provides certain advantages, including that it is objective (e.g., the metric was either satisfied or not satisfied) and easy to visually assess. On the other hand, reporting the results using, for example a relative score, as discussed above, can provide the user with additional information about how close certain metrics were to being met or, conversely, not met. For example, referring again to FIG. 5, if the flow rate data indicated that the flow rate was 4.05 ml/s, this would technically mean the flow rate metric was satisfied, but an individual may wish to know that this metric was close to not being satisfied. A visual indicia, such as a yellow color, which could be used in addition to or alternative to the "thumbs up" icon, could be displayed to indicate that this metric was close to not being satisfied.

The scorecard can also include a summary of the study. The summary can, for example, indicate the number of the metrics satisfied (e.g., 80% or 8/10 of the metrics were satisfied). The scorecard can also provide a grade, such as an "A," "B," or "pass," depending on a user established threshold of metrics that were satisfied. In some non-limiting embodiments, a weighting of the metrics can be provided when defining the metrics for the study such that certain metrics are given more weight in providing a summary of the study on the scorecard. For example, if the "scan range" is a critical parameter of the study, failure to satisfy the scan range metric can mean that the study is automatically assigned a low score, such as an "F" or "fail."

The scorecard can be generated upon request by an individual interested in learning about the study. For example, a technician, doctor, or other individual can request a scorecard for a certain study. Such a request can be made from a remote terminal, such as a reviewing unit, that is connected to the score repository over a network. The request should include sufficient information to identify the database entry for the study of interest. This may include some combination of the patient name, patient ID, study type, study time, and study date. Once the request is made, the necessary data for that study can be extracted from the score repository. The scorecard can then be generated on the remote terminal using software that is local to, or accessible by, the remote terminal. Alternatively, the scorecard can be generated at a different location, such as at a computer associated with the score repository, and then the completed scorecard can be passed to the reviewing unit where it can be presented in a visually perceptible form. This latter approach is particularly advantageous if the reviewing unit is a mobile computing device, such as a tablet or smartphone, that may not have access to the software needed to create a scorecard. In such a situation, the scorecard can be communicated to the reviewing unit in a standard format, such as an Adobe PDF or Microsoft Word file. In one non-limiting embodiment, the scorecards may be automatically generated after the metrics assessment process is complete regardless of whether the scorecard has been requested. In this embodiment, the completed scorecards can be stored in a database from which they can be retrieved.

With reference to Step G of FIG. 1, another manner in which the metrics score can be used is to create an aggregate of the metrics scores from a plurality of studies. The aggregated scores can then be used to generate reports or summaries which can be reviewed by a doctor, technician, hospital review board, or other qualified individual. Determining the studies which are to be included in the aggregate can be accomplished by filtering the available studies through the selection of one or more study characteristics. In one non-limiting embodiment, an aggregate of the metrics scores from a plurality of studies of a certain type can be generated by selecting a certain study type, such as CT pulmonary angiography or CT renal imaging. In another non-limiting embodiment, an aggregate of metrics scores from a certain time period, such as the last six months, or from certain technicians, such as third-shift technicians, can be generated. Multiple filters can be applied simultaneously, such as by selecting studies of a certain type performed in the last six months by third-shift technicians.

For example, an aggregate of the metrics scores for all of the CT pulmonary angiography studies stored in the score repository can be generated. The process of aggregating the metrics scores can include locating all of the entries in the score repository that include data identifying the study as a "CT pulmonary angiography study," extracting at least the metrics scores for each study (including at least data identifying each of the metrics for the study and the scores for each of the metrics), creating a list of the metrics that were analyzed in at least one of the studies, and for each of the metrics in the list, determining how often the metric was satisfied and how often the metric was not satisfied. In some non-limiting embodiments, the listing of metrics can include less than all of the metrics that are identified in at least one of the target studies, such as only those metrics which are most common or only those metrics which are selected in advance of creating the aggregate.

Figure 6:
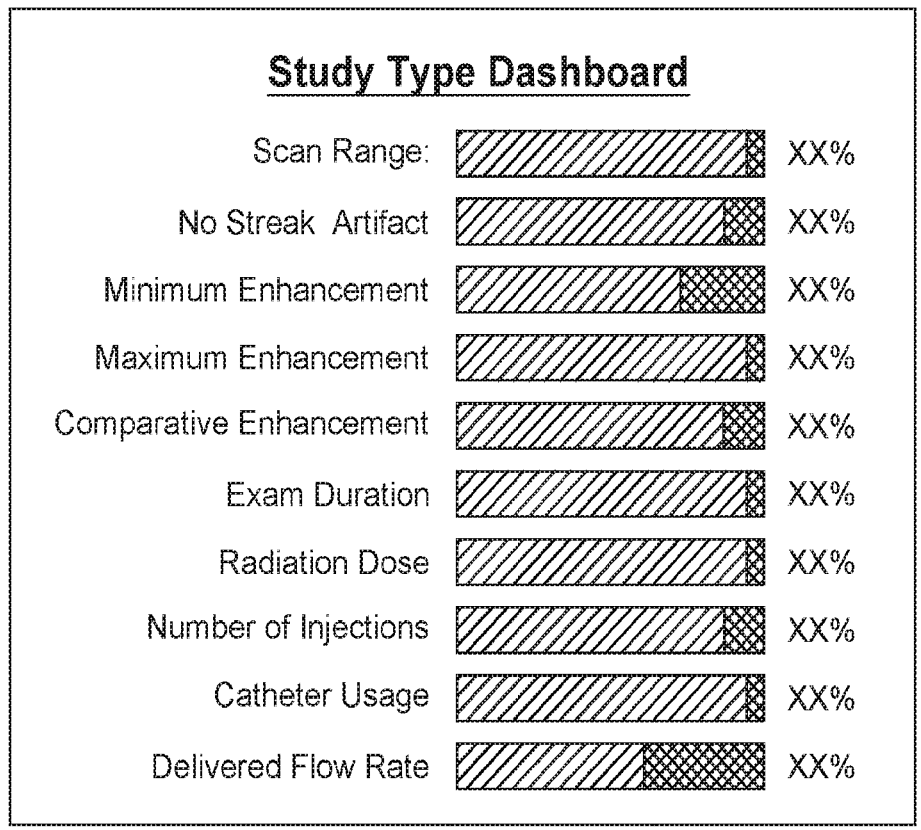
FIG. 6 is a representation of an aggregate of metrics scores presented as a visually perceptible study dashboard according to one non-limiting embodiment.

Once the metrics scores have been aggregated, the resulting data set can be presented in a visually perceptible manner. In one non-limiting embodiment, the aggregate is presented in a "study dashboard," an example of which is illustrated in FIG. 6. With reference to FIG. 6, various metrics are listed on the left-hand side while bar graphs illustrate the relative number of occasions the metric was satisfied (in solid) and not satisfied (in cross-hatch). Also displayed is a calculation of the percentage of the time each metric was satisfied. Additional analyses can be performed, such as associative or cluster analysis done to determine the causal relationships between the metrics. For example, one may observe a correlation between two metrics, which may suggest that there is a common issue that is causing each of the metrics to be met or not met. Some of these correlations may be expected (e.g., a correlation between the injection duration metric and the flow rate metric) while others may not be. Similarly, the absence of an expected correlation, such as the injection duration metric being satisfied at a lower rate than the flow rate metric, may provide insight into the existence of a problem which would otherwise not have been known, such as that the technician was creating an unnecessary delay at the outset of the injection process.

In one non-limiting embodiment, the metrics scores used to create the aggregate can be updated "on the fly" to assess how a change in one or more defined metrics will impact the aggregate data. This process can be used to help determine possible causes for low satisfaction rates for certain metrics. According to this process, a reviewer of the aggregate data, such as a technician or doctor, can select an "update metric" button on his or her terminal. The "update metric" button generates a prompt for the reviewer asking which metric he or she would like to update, presents the current defined metric value, and provides an interface for the reviewer to enter a new value for that metric. Once the new metric value is entered, a new metric assessment process begins with respect to at least the new metric. According to the new metric assessment process, the study data for each of the studies that are part of the aggregate is applied against at least the new metric and a new metrics score for each of the studies is generated. The new metrics scores are then re-aggregated to update the aggregate data. With reference to FIG. 6, this would cause the study dashboard to be updated as well. Storing the study data in a database permits the metrics score for the studies to be recalculated at a later time according to the above process.

The operation of the above feature is further explained with the following non-limiting example. In the study dashboard in FIG. 6, the minimum enhancement and delivered flow rate metrics have satisfaction rates that are lower than the other metrics. A possible cause of this is that the catheters used for the studies were too small, thus limiting the flow rate that could be achieved and preventing enough contrast from reaching the patient to meet the minimum enhancement value. A reviewer may be interested in understanding if, in fact, the catheter size is the root cause of this issue. Again with reference to FIG. 6, the reviewer would recognize that one of the study metrics is the catheter usage metric of "catheter is 18-, 20-, or 22-gauge." The reviewer could then redefine this metric to see how the dashboard would change if the catheter usage metric was instead "catheter is 18- or 20-gauge." Upon redefining the catheter usage metric, the system would perform another metrics assessment on each of the studies at least for the catheter usage metric. As explained above, this would involve, for each of the studies, applying the newly defined metric to the study data for that study. Once the metrics assessment is complete, the new metrics score for each of the studies could again be aggregated and presented in an updated study dashboard. Since the new catheter usage metric is more difficult to satisfy than the original metric by virtue of the list of acceptable catheter sizes becoming smaller, one would expect to see a change in the aggregate of the catheter usage metric to reflect that the metric was satisfied on fewer occasions. If, however, one did not see any change in this aggregate, or only a slight change in this aggregate, one could infer that none of the studies, or only a limited number of the studies, used a 22-gauge catheter. This would suggest that the root cause of the low satisfaction rate for the delivered flow rate and minimum enhancement metrics is not the catheter size. On the other hand, if a change in the aggregate of the catheter usage metric was observed, and the updated catheter usage metric satisfaction rate coincided closely with the satisfaction rates for the delivery flow rate and minimum enhancement metrics, the reviewer could infer a causal relationship between the use of a 22-gauge catheter and unsatisfactory flow rate and minimum enhancement.

With reference to Step H, analysis of the metrics scores for one or more studies can be used to determine whether there are potential changes that can or should be made to the study protocols in order to improve the performance thereof. In the above example, analysis of the catheter usage metric could determine a potential source of a low satisfaction rate of the flow rate and minimum enhancement metrics. If this analysis demonstrates that the use of a 22-gauge catheter is a likely root cause of the low satisfaction rates for the flow rate and minimum enhancement metrics, a reviewer of this information can recommend that the study protocol for the study type at issue, in this case CT pulmonary angiography, or even other similar types of studies, be modified to permit only catheter sizes of 18- or 20-gauge. As mentioned above, for purposes of this disclosure, a study protocol is a structured set of criteria to guide the technologist on how to conduct a certain imaging study. Thus, with reference to Step I, the recommendations that can flow from the process described herein can be implemented by updating the criteria that are part of the study protocol at issue. In the example above, the reviewer could modify the catheter size criteria for the protocol so that the technician or other medical personnel tasked with conducting a CT pulmonary angiography study in the future is guided to a catheter size that is more likely to allow the desired flow rate and minimum enhancement metric values to be reached. The recommendations could also be presented as part of a larger policy change at the hospital or other organization regarding, for example, the use of certain catheter sizes in general. In one embodiment, rather than relying on human intuition and ad-hoc analysis for discovering casual relationships, various computer techniques (e.g., gradient descent optimizations, k-Nearest Neighbor, Principle Component Analysis, or other heuristic or brute force optimization algorithms) could be applied to automatically bring forward suspected causes for human review and consideration.

The systems and methods described herein can provide a mechanism that uses data generated during the ordinary course of performing imaging studies to continuously improve upon the protocols used to perform these studies. As mentioned above, based upon one or more recommendations generated through the analysis of metrics scores, recommendations can be made to update one or more study protocols and create improved study protocols. These improved study protocols can then be used as the defined study protocols for future studies. Use of these improved study protocols as, for example, the study protocols defined in Step A of FIG. 1, can "close the loop" and provide a way in which data from previous studies can help develop improved protocols that can be used to conduct subsequent studies which can generate additional data that can help develop even further improved protocols.

Figure 7:
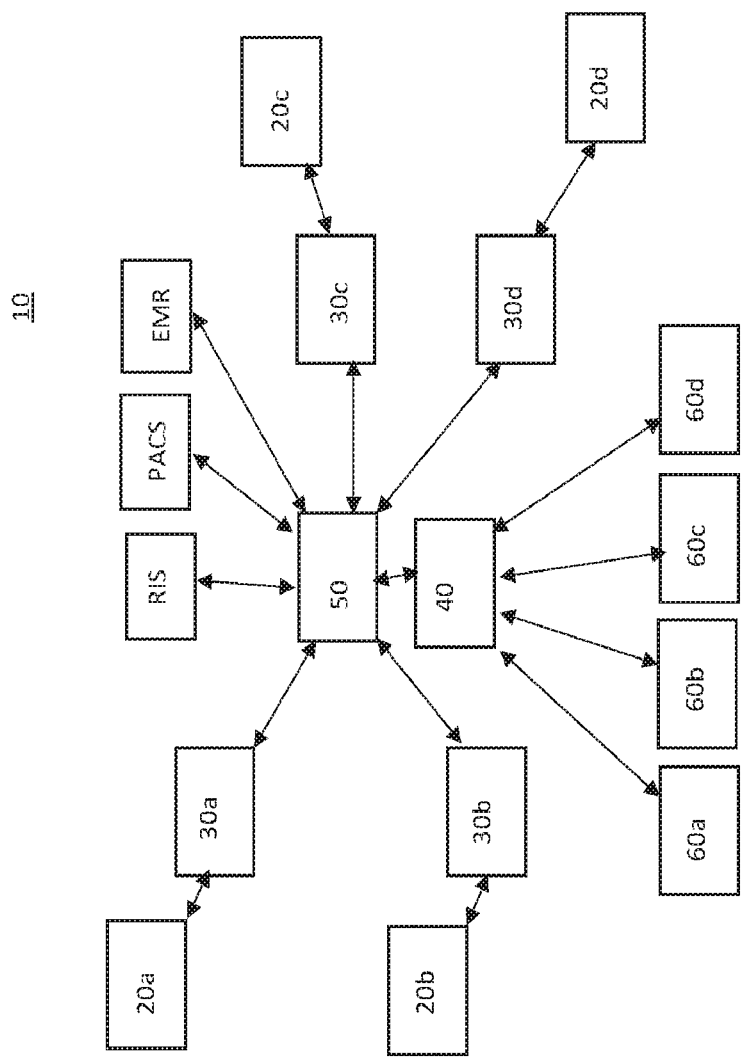
FIG. 7 is a schematic view of a system according to one non-limiting embodiment.

FIG. 7 illustrates a system 10 according to one embodiment. System 10 can include one or more protocol units 20a-d for defining study protocols and the study metrics associated with the study protocols. System 10 can also include one or more imaging suites 30a-d for performing imaging studies according to the defined protocols. System 10 may also include a scoring unit 40 for performing metrics assessments on the studies. System 10 can also include at least one score repository 50 for storing data associated with the studies, including the metrics scores and at least some of the data used to generate the metrics scores. System 10 can also include one or more reviewing units 60a-d for reviewing and/or analyzing one or more metrics scores stored in the score repository 50 and generating scorecards and dashboards, as well as other reports and aggregates, of the data stored in the score repository 50 and presenting these reports and aggregates in a visually perceptible manner. However, these functions, including those associated with analyzing the one or more metrics scores stored in the score repository 50, can also be performed on the scoring unit 40.

Each of the protocol units 20a-d, scoring unit 40, and reviewing units 60a-d can be in the form of a terminal, such as a server or other computer comprised of hardware and software, having an associated processor (or series of processors) and non-transitory, computer readable storage medium that is in operable communication with the processor such that the processor can execute programming instructions stored in the storage medium so as to perform the functions associated with each unit. In some non-limiting embodiments, the protocol units 20a-d, scoring unit 40, and/or reviewing unit 60a-d may be combined into a single terminal where the functionality of each unit is embodied as a set of programming instructions stored in a non-transitory medium associated with the terminal. In other embodiments, these units are in the form of separate terminals or any other combination of hardware and/or software components. The individual units of system 10 may be localized or, in some embodiments, distributed among any number of hardware devices, local or remote, preferably in communication with one another. Further, each unit may itself be comprised of a distributed system, such as a series of servers and/or computers.

By way of example, the protocol units 20a-d, scoring unit 40, and/or reviewing units 60a-d may be incorporated into pre-existing hardware and/or software associated with the imaging suites 30a-d and/or other workstations located in a medical facility. By way of another example, each of the protocol units 20a-d and the reviewing units 60a-d may be in the form of a stand-alone workstation that is used by medical personnel, or they may be comprised of software that can be installed on a mobile computing device such as a tablet or smartphone. The score repository 50 can be in the form of a database, such as a database comprised of a plurality of records where each record relates to a single study, and the scoring unit 40 can be in the form of a computer associated with the score repository 50. Each of the units of the system 10, including the score repository 50 and the imaging suites 30a-d, can communicate with one another and with other systems that are typically part of a medical imaging facility, such as PACS, RIS, EMR, and HIS, so that data can be transferred between the various systems. It will be appreciated that other arrangements are possible.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

The invention claimed is:

1. A method, comprising:
  for each of a plurality of imaging studies, defining, at a protocol unit, a study protocol comprising a set of criteria regarding how to conduct the imaging study using an injector and scanner;
  for each of the plurality of imaging studies, defining, at the protocol unit, a set of study metrics;

for each of the plurality of imaging studies, performing the defined study protocol so as to generate data associated with a result of the imaging study;

for each of the plurality of imaging studies, performing, by a scoring unit, a metrics assessment by applying at least a portion of the data associated with the result of the imaging study against the set of study metrics for the imaging study so as to generate a metrics score for the imaging study, wherein the metrics score for each of the plurality of imaging studies is stored in a score repository;

aggregating the metrics scores for the plurality of imaging studies to generate an aggregated metrics score;

for each of the plurality of imaging studies, performing, by the scoring unit, an updated metrics assessment, comprising selecting an updated value for at least one of the study metrics and applying at least a portion of the data associated with the result of the imaging study against the updated value so as to generate an updated metrics score for the imaging study;

aggregating the updated metrics scores for the plurality of imaging studies to generate an updated aggregated metrics score;

reviewing, at a reviewing unit, the aggregated metrics score and updated aggregated metrics score;

based on the review of the aggregated metrics score and updated aggregated metrics score, generating at least one updated study protocol comprising an updated set of criteria regarding how to conduct an imaging study using an injector and scanner; and performing a subsequent imaging study based upon the at least one updated study protocol so as to generate data associated with a result of the subsequent imaging study.

2. The method of claim 1, wherein the plurality of imaging studies are selected from the group consisting of computerized tomography imaging studies, positron emission tomography imaging studies, molecular imaging studies, ultrasound imaging studies, and magnetic resonance imaging studies.

3. The method of claim 1, wherein the set of study metrics comprises a list of quantifiable characteristics of the study and the results thereof.

4. The method of claim 1, wherein defining the set of study metrics comprises selecting a plurality of study metrics from a list of available study metrics.

5. The method of claim 4, wherein defining the set of study metrics further comprises providing, for each of the plurality of study metrics, a metric evaluation criteria.

6. The method of claim 1, wherein reviewing the aggregated metrics score and updated aggregated metrics score comprises reviewing a visually perceptible summary of the aggregated metrics score and updated aggregated metrics score.

7. A method, comprising:
receiving, at a score repository, data related to a plurality of imaging studies, wherein the data related to the plurality of imaging studies comprises, for each of the plurality of imaging studies, a study protocol comprising a set of criteria regarding how to conduct the imaging study using an injector and scanner, a set of study metrics, and data associated with a result of performing the study protocol for the imaging study;

performing, by a scoring unit, a metrics assessment for each of the plurality of imaging studies by applying at least a portion of the data associated with the result of the imaging study against the set of study metrics for the imaging study so as to generate a metrics score for the imaging study;

receiving, at a reviewing unit, a visually perceptible summary of the metrics score for at least one of the plurality of imaging studies; and presenting, on one or more display screens, the visually perceptible summary of the metrics score for the at least one of the plurality of imaging studies;

generating, by the scoring unit, an aggregate of the metrics scores comprised of a plurality of the metrics scores;

receiving, at the reviewing unit, a visually perceptible summary of the aggregate of the metrics scores;

presenting, on one or more display screens, the visually perceptible summary of the aggregate of metrics scores;

receiving, at the scoring unit, a request to modify one or more of the study metrics used to generate one or more of the metrics scores included in the aggregate of the metrics scores;

generating, by the scoring unit, one or more updated metrics scores by applying at least a portion of the data associated with the result of the imaging study against at least the one or more modified study metrics;

generating, by the scoring unit, an updated aggregate of the metrics scores comprised of at least the updated metrics scores;

based on the aggregate of the metrics scores and the updated aggregate of the metrics scores, generating at least one updated study protocol comprising an updated set of criteria regarding how to conduct an imaging study using an injector and scanner; and performing a subsequent imaging study based upon the at least one updated study protocol so as to generate data associated with a result of the subsequent imaging study.

8. The method of claim 7, further comprising:
receiving, at the reviewing unit, a visually perceptible summary of the updated aggregate of the metrics scores; and presenting, on one or more display screens, the visually perceptible summary of the updated aggregate of the metrics scores.

9. The method of claim 7, wherein the set of study metrics comprises a list of quantifiable characteristics of the study and the results thereof.

10. The method of claim 7, wherein the visually perceptible summary of the metrics score comprises a set of binary indicators, wherein each binary indicator is associated with a study metric.

11. A system, comprising:
one or more protocol units, wherein each of the protocol units has associated therewith a non-transitory, computer readable medium containing a set of programming instructions that, when executed by a processor, permit the protocol unit to define, for each of a plurality of imaging studies, a study protocol and a set of study metrics, wherein the study protocol comprises a set of criteria regarding how to conduct the imaging study using an injector and scanner;

a score repository comprising a set of database entries, wherein each database entry is associated with one of the plurality of imaging studies and comprises the study protocol for the imaging study, the set of study metrics for the imaging study, and data associated with a result of performing the study protocol for the imaging study;

one or more scoring units, wherein each of the scoring units has associated therewith a non-transitory, computer readable medium containing a set of programming instructions that, when executed by a processor, permit the scoring unit to perform, for each of the plurality of imaging studies, a metrics assessment by applying at least a portion of the data associated with the result of the imaging study against the set of study metrics for the imaging study so as to generate a metrics score for the imaging study, wherein the programming instructions, when executed by a processor, further permit the scoring unit to aggregate the metrics scores for the plurality of imaging studies to generate an aggregated metrics score, receive an updated value for at least one of the study metrics, apply, for each of the plurality of imaging studies, at least a portion of the data associated with the result of the imaging study against the updated value so as to generate an updated metrics score for the imaging study, and aggregate the updated metrics scores for the plurality of imaging studies to generate an updated aggregated metrics score;

one or more reviewing units, wherein each of the reviewing units has associated therewith a non-transitory, computer readable medium containing a set of programming instructions that, when executed by a processor, permit the reviewing unit to display a visually perceptible summary of the aggregated metrics score and updated aggregated metrics score on a display screen associated with the reviewing unit, wherein the programming instructions, when executed by a processor, further permit the reviewing unit to generate at least one updated study protocol based on a review of the aggregated metrics score and the updated aggregated metrics score, the at least one updated study protocol comprising an updated set of criteria regarding how to conduct an imaging study using an injector and scanner; and at least one of an injector and a scanner that operate according to the at least one updated study protocol.

* * * * *